United States Patent [19]
Schwager

[11] Patent Number: 5,954,672
[45] Date of Patent: Sep. 21, 1999

[54] CONTROLLED GAP GUIDEWIRE

[75] Inventor: Michael Schwager, Winterthur, Switzerland

[73] Assignee: Schneider (Europe) GmbH, Switzerland

[21] Appl. No.: 08/989,321

[22] Filed: Dec. 11, 1997

[30] Foreign Application Priority Data

May 21, 1997 [EP] European Pat. Off. .............. 97108244

[51] Int. Cl.$^6$ ....................................................... A61B 5/00
[52] U.S. Cl. .......................................................... 600/585
[58] Field of Search .................... 600/433–436, 600/585

[56] References Cited

U.S. PATENT DOCUMENTS

| | | | |
|---|---|---|---|
| 4,003,369 | 1/1977 | Heilman et al. ............................ | 128/2 |
| 4,080,706 | 3/1978 | Heilman et al. ........................... | 29/173 |
| 4,721,117 | 1/1988 | Mar et al. ................................. | 128/772 |
| 4,724,846 | 2/1988 | Evans, III ................................. | 128/772 |
| 4,779,628 | 10/1988 | Machek .................................... | 128/772 |
| 4,854,330 | 8/1989 | Evans, III et al. ....................... | 128/772 |
| 4,895,168 | 1/1990 | Machek .................................... | 128/772 |
| 4,922,924 | 5/1990 | Gambale et al. ........................ | 128/772 |
| 4,953,553 | 9/1990 | Tremulis .................................. | 128/637 |
| 4,964,409 | 10/1990 | Tremulis .................................. | 128/657 |
| 4,971,490 | 11/1990 | Hawkins .................................. | 128/772 |
| 5,050,606 | 9/1991 | Tremulis .................................. | 128/637 |
| 5,063,935 | 11/1991 | Gambale .................................. | 128/657 |
| 5,069,226 | 12/1991 | Yamauchi et al. ....................... | 128/772 |
| 5,127,917 | 7/1992 | Niederhauser et al. ................. | 606/191 |
| 5,129,890 | 7/1992 | Bates et al. .............................. | 604/281 |
| 5,171,383 | 12/1992 | Sagaye et al. ........................... | 148/564 |
| 5,267,574 | 12/1993 | Viera et al. .............................. | 128/772 |
| 5,345,945 | 9/1994 | Hodgson et al. ........................ | 128/772 |
| 5,376,083 | 12/1994 | Mische .................................... | 604/264 |
| 5,380,307 | 1/1995 | Chee et al. ............................... | 604/264 |
| 5,404,886 | 4/1995 | Vance ....................................... | 128/772 |
| 5,425,724 | 6/1995 | Akins ....................................... | 604/284 |
| 5,429,139 | 7/1995 | Sauter ...................................... | 128/772 |
| 5,458,585 | 10/1995 | Salmon et al. .......................... | 604/280 |
| 5,511,559 | 4/1996 | Vance ....................................... | 128/772 |
| 5,527,292 | 6/1996 | Adams et al. ........................... | 604/171 |
| 5,527,298 | 6/1996 | Vance et al. ............................. | 604/280 |
| 5,569,197 | 10/1996 | Helmus et al. .......................... | 604/96 |
| 5,605,163 | 2/1997 | Hani ......................................... | 128/772 |
| 5,617,875 | 4/1997 | Schwager ................................. | 128/772 |
| 5,706,826 | 1/1998 | Schwager ................................. | 600/585 |

FOREIGN PATENT DOCUMENTS

| | | |
|---|---|---|
| 0313836 A3 | 5/1989 | European Pat. Off. . |
| 0405823 A2 | 1/1991 | European Pat. Off. . |
| 0652026 A1 | 5/1995 | European Pat. Off. . |
| 0729765 A1 | 9/1996 | European Pat. Off. . |
| 0738495 A1 | 10/1996 | European Pat. Off. . |
| 0750879 A1 | 1/1997 | European Pat. Off. . |

*Primary Examiner*—Max Hindenburg
*Attorney, Agent, or Firm*—Crompton, Seager & Tufte, LLC

[57] ABSTRACT

The guidewire comprises an elongated flexible shaft which is tubular. A coil assembly comprises a first coil having a proximal portion with a peripheral size providing an unstressed fit within the distal portion of shaft. Tight recesses formed between consecutive turns of the coil by a solder filler hold adhesive between the coil and the tubular shaft.

11 Claims, 2 Drawing Sheets

CONTROLLED GAP GUIDEWIRE

BACKGROUND OF THE INVENTION

This application claims priority under 35 U.S.C. § 119 of European Patent Application No. 97108244.1 filed in the European Patent Office on May 21, 1997.

This invention relates to guidewires as commonly used for positioning catheters through blood vessels or for detecting blood pressure in vascular configurations.

Typically a guiding catheter may be inserted through the vasculature and the guidewire is inserted into a blood vessel via the guiding catheter. A balloon catheter may then be pushed over the guidewire for proper location into the blood vessel; alternatively, where the guidewire is for use with a pressure measuring equipment, the guidewire allows detection of the blood pressure, for example in the vicinity of a stenosis.

Usually, the distal end of the guidewire is shapeable to conform with the tortuous pathways of the blood vessels, and the shaft of the guidewire must have a good kink resistance to assure pushability of the guidewire and the transmission of torque thereto. A further requirement is that the distal end of the guidewire be radiopaque to allow tracking of the guidewire along the vasculature.

More specifically, this invention is directed to a guidewire comprising an elongated flexible shaft with a proximal portion and a distal tubular portion, a coaxial coil assembly at the distal portion of said shaft, said coaxial coil assembly comprising a first coil having a proximal portion and a distal portion, the proximal portion of said first coil being inserted into the distal tubular portion of the shaft, a second coil having a proximal portion joined to the distal portion of the first coil and a distal portion terminating into a tip, and an adhesive bond for the proximal portion of the first coil in the distal tubular portion of the shaft.

A guidewire of that kind is described in EP 0 729 765 A1. In the guidewire of that document, the proximal portion of the first coil is threadedly force fitted into the tubular distal portion of the shaft, whereby the first coil makes a thread way into the tubular distal portion of the shaft. In one embodiment, the proximal portion of the first coil has adjacent windings that are spaced apart in order to facilitate the threadingly fitting into the tubular portion of the shaft. This configuration also allows the sucking and full penetration of an adhesive into the proximal portion of the coil to secure the definite locking of the proximal portion of the coil in the distal portion of the shaft.

This guidewire results in a shape conforming assembly which has all the advantages of a threaded assembly without the need to specially machine a thread in the tubular portion of the shaft. And as the first coil makes the thread way into the tubular portion of the shaft, the assembly is largely tolerance free, of course within the limits of a given range of tolerances. However, if the assembly between the proximal portion of the first coil and the tubular portion of the shaft exceeds the limits of the tolerances admitted for the assembly, there may be problems in securing the assembly. If the outer diametral size of the proximal portion of the first coil is too largely bigger than the inner diameter of the tubular portion of the shaft, there may be difficulties to threadedly insert the proximal portion of the first coil into the tubular portion of the shaft, with the risk of breaking the coil or of damaging the shaft upon doing so. When the outer diametral size of the proximal portion of the first coil is smaller than the inner diameter of the tubular portion of the shaft, the threading engagement of the coil in the tubular shaft cannot be secured; and in that case, the adhesive which is sucked and fully penetrates into the proximal portion of the first coil cannot safely help in securing the assembly.

All documents cited herein, including the foregoing, are incorporated herein by reference in their entireties for all purposes.

SUMMARY OF THE INVENTION

It is an object of this invention to improve over the cited art by means of a guidewire which is easy to manufacture while assuring safe connection between the coil assembly and the tubular portion of the shaft in a wide range of coil and shaft tolerances. A further object of the invention is a guidewire that is versatile and provides excellent qualities of pushability and shapeability.

Accordingly, when the proximal portion of the first coil has a peripheral size providing a fit of the proximal portion of the first coil within the distal tubular portion of the shaft, wherein pocket means formed around and integral with the proximal portion of the first coil hold adhesive of the adhesive bond between the periphery of the proximal portion of the first coil and the distal tubular portion of the shaft, the proximal portion of the first coil is merely inserted plug like into the distal tubular portion of the shaft and the pocket means provide a tight retention for the adhesive where it is needed, between the periphery of the coil and the inner wall of the tubular portion of the shaft. There is always the required minimum layer thickness for the adhesive to secure a safe adhesive connection in a wide range of coil and tubular shaft tolerances. The adhesive cannot flow inside the coil and weaken the adhesive bond of the coil into the tubular shaft. Insertion of the coil into the tubular shaft is effortless and there are no risks of coil breaking or shaft damaging. The assembly is stress free as long as the coil can be loosely inserted into the tubular shaft, the coil and shaft can be safely secured and the assembly becomes fail proof. Manufacture of the elements of the assembly is greatly simplified as it avoids narrow tolerances which are always difficult to respect in tiny parts. The shaft may be designed at will for best flexibility and kinking resistance, with an optimal choice in varying diameters and thickness for flexibility control. And of course, the shaft may be tubular only at its distal portion or fully tubular as would be required for use in pressure measuring equipment.

When the pocket means are formed by outwardly oriented tight recesses between consecutive turns of the proximal portion of the first coil, advantage can be taken of the intrinsic outer shape of the coil. And when the proximal portion of the first coil has consecutive turns spaced apart from one another and said pocket means are formed by outwardly oriented tight recesses between said spaced apart consecutive turns, a larger retention is assured for the adhesive to further improve ease and safety of the adhesive bonding.

The pocket means may be advantageously and simply formed by filler means between consecutive turns of the proximal portion of the first coil. And for further ease of manufacture, such filler means may also extend through the distal portion of the first coil, with the proximal portion of the second coil overlapping the distal portion of the first coil and bonded thereto by said filler means. In that environment, the distal portion of the first coil and the proximal portion of the second coil may both have consecutive turns spaced apart from one another and in threaded engagement with each other to facilitate positioning of the second coil on the first coil and insertion of the filler means therebetween.

When core means extend through the first coil wherein said first coil is bonded to said core means by said filler means, the pocket means are obtained by mere introduction of the filler means between consecutive turns of the proximal portion of the first coil as the core means act as a support for the filler means forming the pocket means. And when the core means also extend through the second coil and terminate into a tip terminating the distal portion of the second coil, a complete and sturdy coil assembly may be prepared as a unit which will then be affixed to the shaft, thereby preventing unwanted manipulation of the shaft during pre-assembly of the coils.

Preferably, the filler means are formed by solder. However, the filler means may also be formed by glue.

In sum, the invention relates to a guidewire including an elongated flexible shaft with a proximal portion and a distal tubular portion, a coaxial coil assembly at the distal portion of the shaft. The coaxial coil assembly includes a first coil having a proximal portion and a distal portion. The proximal portion of the first coil is inserted into the distal tubular portion of the shaft. A second coil having a proximal portion is joined to the distal portion of the first coil and a distal portion terminates into a tip. An adhesive bond for the proximal portion of the first coil is in the distal tubular portion of the shaft. The proximal portion of the first coil has a peripheral size providing a fit of the proximal portion of the first coil within the distal tubular portion of the shaft. The pocket means formed around and integral with the proximal portion of the first coil hold adhesive of the adhesive bond between the periphery of the proximal portion of the first coil and the distal tubular portion of the shaft. The pocket means may be formed by outwardly oriented tight recesses between consecutive turns of the proximal portion of the first coil. The proximal portion of the first coil may have consecutive turns spaced apart from one another and the pocket means are formed by outwardly oriented tight recesses between the spaced apart consecutive turns. The pocket means may be formed by filler means between consecutive turns of the proximal portion of the first coil. The filler means may extend through the distal portion of the first coil, and the proximal portion of the second coil may be overlapping the distal portion of the first coil and bonded thereto by the filler means. The distal portion of the first coil and the proximal portion of the second coil both may have consecutive turns spaced apart from one another and in threaded engagement with each other. The guidewire may further include core means extending through the first coil wherein the first coil is bonded to the core means by the filler means. The core means may also extend through the second coil and terminate into the tip terminating the distal portion of the second coil. The filler means may be formed by solder. The filler means may be formed by glue.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DETAILED DESCRIPTION OF THE INVENTION

Figure 1:
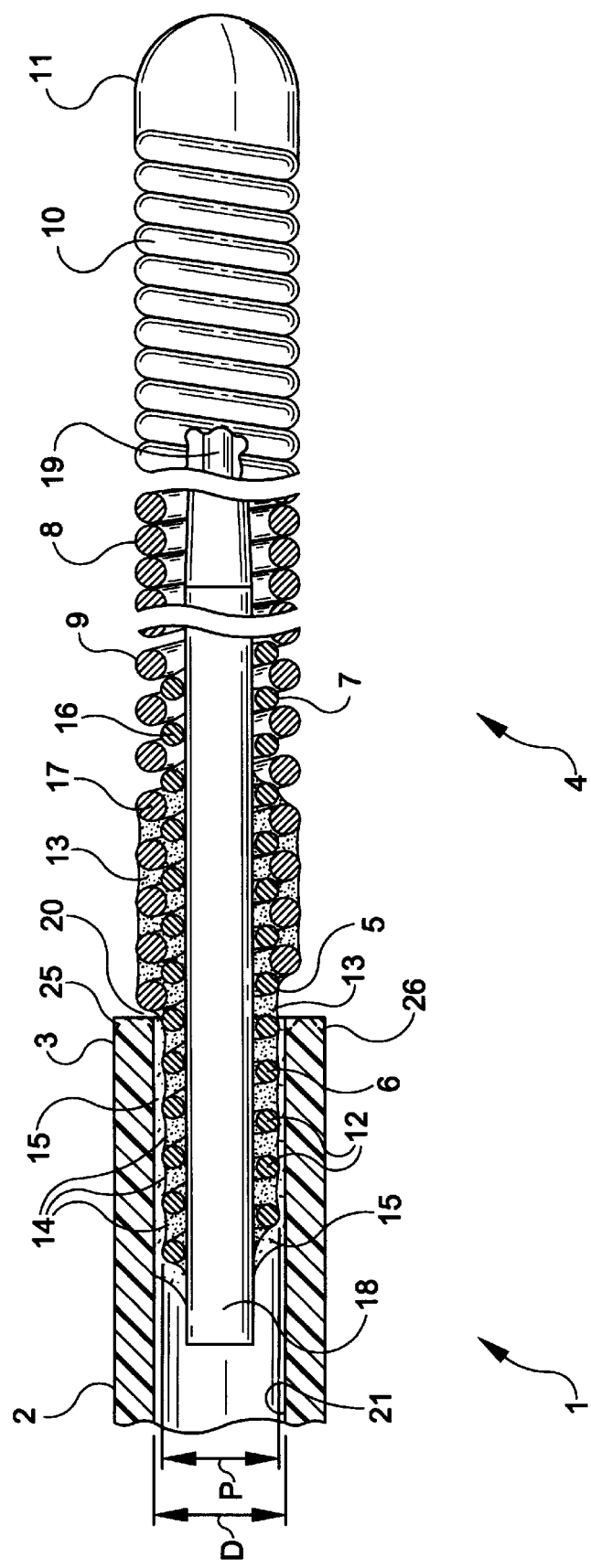
FIG. 1 is a cross sectional view along the longitudinal axis of the guidewire.

The guidewire 1 comprises an elongated flexible shaft 2 having a proximal portion (not shown) and a distal portion 3. As shown, the distal portion 3 is tubular.

Preferably, the shaft is made of an elastic Nickel Titanium alloy. Other materials such as for example plastic materials are also possible.

A coaxial coil assembly 4 is affixed to the distal portion 3 of shaft 2. This coil assembly comprises a first coil 5 having a proximal portion 6 and a distal portion 7, and a second coil 8 having a proximal portion 9 and a distal portion 10 ending into a brazed tip 11. Preferably, both coils 5 and 8 are made of a high density metal, such as for example Tungsten, for radiopacity purposes.

The proximal portion 6 of the first coil 5 has a peripheral size P smaller than the inner diameter D of the distal portion 3 of shaft 2, thereby providing an unstressed fit for the proximal portion 6 of the first coil 5 within the distal portion 3 of shaft 2.

The consecutive turns 12 of the proximal portion 6 of the first coil 5 are spaced apart from one another and a solder filler 13 between said consecutive turns forms outwardly oriented tight recesses 14 around and integral with the proximal portion 6 of first coil 5. An adhesive 15 is inserted in recesses 14 which hold the adhesive 15 between the periphery of the proximal portion 6 of the first coil 5 and the inner wall 21 of distal tubular portion 3 of shaft 2.

The consecutive turns 16 of the distal portion 7 of first coil 5 are spaced apart from one another and the consecutive turns 17 of the proximal portion 9 of the second coil 8, also spaced apart from one another, are in threaded engagement with the turns 16 of first coil 5. The solder filler 13 extends through the distal portion 7 of first coil 5 and through the proximal portion 9 of second coil 8 thereby bonding the second coil to the first coil.

A cylindrical flexible core 18, for example of stainless steel, extends through the first coil 5 which is bonded thereto by the solder filler 13. The core 18 also extends through the second coil 8 where it tapers as at 19 for termination (not shown) in brazed tip 11.

Figure 2:
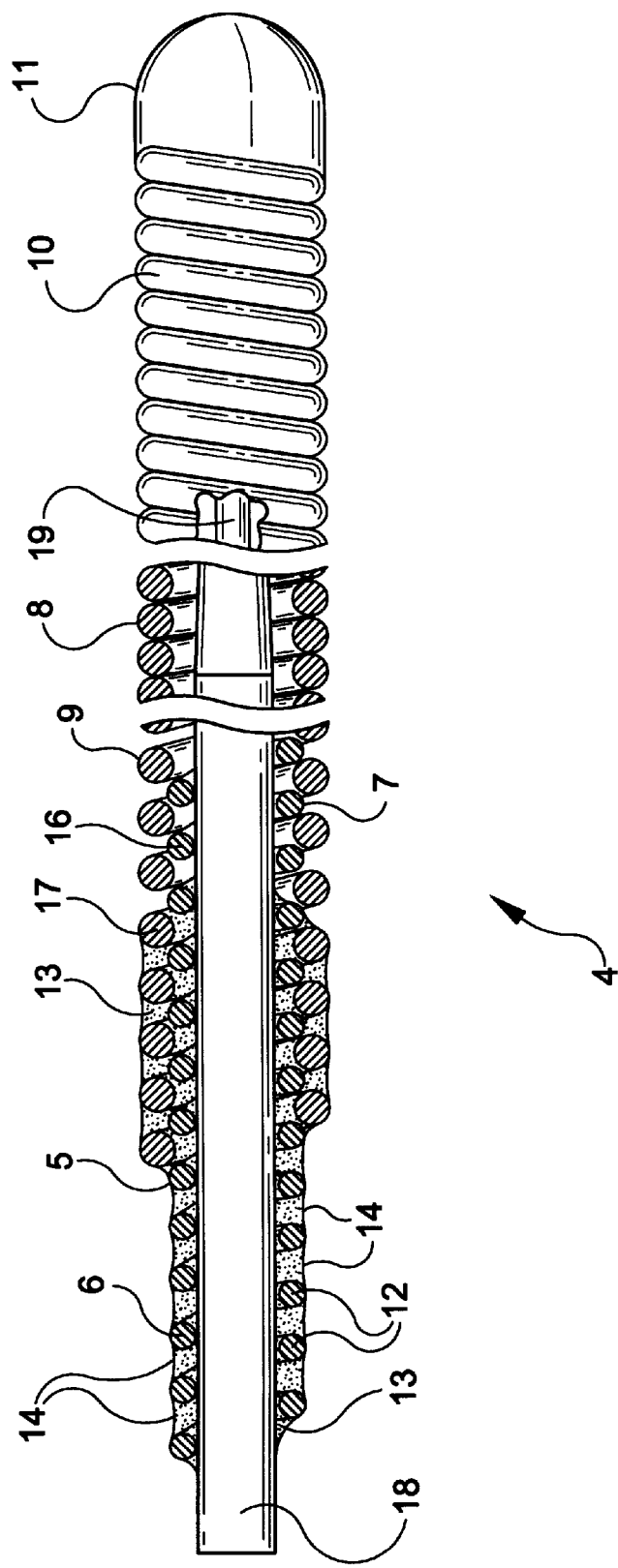
FIG. 2 is a detail of FIG. 1.

As shown in FIG. 2, the assembly of the two coils 5 and 8 via solder filler 13 and core 18 forms a unit ready for fixture to the shaft 2 by means of adhesive 15.

Variants are available without departing from the scope of the invention. For example, the consecutive turns 12 of the proximal portion 6 of first coil 5 need not be spaced apart from one another to form the tight recesses 14; they can be close to one another. Same, the consecutive turns 16 of the distal portion 7 of first coil 5 and the consecutive turns 17 of the proximal portion 9 of second coil 8 may be close to one another.

The pocket effect for the adhesive 15 assured by the solder filler 13 between the turns of coil 5 may be achieved by a tubular layer of tight material, for example a plastic material, affixed within coil 5. Also the pocket effect assured by recesses 14 may be obtained by a recessed layer of tight material affixed to and surrounding the first coil 5.

The core 18 may be suppressed or limited to the first coil or to the first coil and area of bonding of the two coils. The solder filler 13 may be replaced by a glue filler. The shaft 2 may be completely tubular or tubular only at its distal end 3.

As shown in FIG. 1, there is a gap 20 between the proximal portion 9 of second coil 8 and the distal portion 3 of shaft 2. This gap may be reduced.

In the example shown, coil 8 has a smaller outer diameter than the outer diameter of shaft 2. Both elements could have substantially the same outer diameter for a smooth transition at the junction area.

In the example shown, the distal inner and outer edges of shaft 2 are square. It would be however preferable to have the outer edge of shaft 2 rounded as shown in dotted lines at 25 in FIG. 1, and also to have the inner edge of shaft 2 chamfered as shown in dotted lines at 26 in FIG. 1, whereas a better repartition of the adhesive 15 at that level.

The peripheral size P of first coil 5 may be equal to or slightly less than the inner diameter D of the distal portion 3 of shaft 2. The two coils 5 and 8 may not be in overlapping condition.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A guidewire comprising:

an elongated flexible shaft having a proximal portion and a distal tubular portion;

a coaxial assembly at the distal portion of the shaft, the coaxial coil assembly including a first coil having a proximal portion and a distal portion, the proximal portion of the first coil being inserted into the distal tubular portion of the shaft, a second coil having a proximal portion joined to the distal portion of the first coil and a distal portion terminating into a tip; and an adhesive bond for the proximal portion of the first coil in the distal tubular portion of the shaft, wherein the proximal portion of the first coil has a peripheral size providing a fit of the proximal portion of the first coil within the distal tubular portion of the shaft such that the adhesive bond is disposed at least in part within a gap defined between the first coil and the shaft.

2. A guidewire according to claim 1, further comprising pocket means formed with the proximal portion of the first coil to hold adhesive.

3. The guidewire according to claim 2, wherein the pocket means are formed by outwardly oriented tight recesses between consecutive turns of the proximal portion of the first coil.

4. The guidewire according to claim 2, wherein the proximal portion of the first coil has consecutive turns spaced apart from one another and the pocket means are formed by outwardly oriented tight recesses between the spaced apart consecutive turns.

5. The guidewire according to claim 2, wherein the pocket means are formed by filler means between consecutive turns of the proximal portion of the first coil.

6. A guidewire according to claim 5, wherein the filler means extend through the distal portion of the first coil, and the proximal portion of the second coil is overlapping the distal portion of the first coil and bonded thereto by the filler means.

7. The guidewire according to claim 6, wherein the distal portion of the first coil and the proximal portion of the second coil both have consecutive turns spaced apart from one another and in threaded engagement with each other.

8. The guidewire according to claim 5, further comprising core means extending through the first coil wherein the first coil is bonded to the core means by the filler means.

9. The guidewire according to claim 8, wherein the core means also extend through the second coil and terminate into the tip terminating the distal portion of the second coil.

10. The guidewire according to claim 5, wherein the filler means are formed by solder.

11. The guidewire according to claim 5, wherein the filler means are formed by glue.

* * * * *